US011412921B2

(12) United States Patent
Holsten

(10) Patent No.: US 11,412,921 B2
(45) Date of Patent: Aug. 16, 2022

(54) MULTI LUMEN ACCESS DEVICE

(71) Applicant: Covidien LP, Mansfield, MA (US)

(72) Inventor: Henry E. Holsten, Hamden, CT (US)

(73) Assignee: Covidien LP, Mansfield, MA (US)

( * ) Notice: Subject to any disclaimer, the term of this patent is extended or adjusted under 35 U.S.C. 154(b) by 108 days.

(21) Appl. No.: 16/776,994

(22) Filed: Jan. 30, 2020

(65) Prior Publication Data

US 2020/0163541 A1 May 28, 2020

Related U.S. Application Data

(63) Continuation-in-part of application No. 16/149,479, filed on Oct. 2, 2018.

(51) Int. Cl.
*A61B 1/12* (2006.01)
*A61B 90/70* (2016.01)
*A61B 1/00* (2006.01)
*A61L 2/16* (2006.01)

(52) U.S. Cl.
CPC .......... *A61B 1/126* (2013.01); *A61B 1/00112* (2013.01); *A61B 90/70* (2016.02); *A61L 2/16* (2013.01); *A61B 2090/701* (2016.02); *A61L 2202/24* (2013.01)

(58) Field of Classification Search
CPC .... A61B 2017/3449; A61B 2017/3447; A61B 2017/3445; A61B 17/3423; A61B 1/12
See application file for complete search history.

(56) References Cited

U.S. PATENT DOCUMENTS

| | | | |
|---|---|---|---|
| 3,189,223 | A | 6/1965 | Mackal |
| 3,206,784 | A | 9/1965 | Linenfelser |
| 3,258,809 | A | 7/1966 | Harvey |
| 3,840,145 | A | 10/1974 | Almanza |
| 4,114,668 | A | 9/1978 | Hickey |
| 4,281,646 | A | 8/1981 | Kinoshita |
| 4,919,113 | A | 4/1990 | Sakamoto et al. |
| 4,941,872 | A | 7/1990 | Felix et al. |
| 5,127,909 | A | 7/1992 | Shichman |

(Continued)

FOREIGN PATENT DOCUMENTS

| | | |
|---|---|---|
| DE | 202008009527 U1 | 10/2008 |
| DE | 2008059633 | 6/2010 |

(Continued)

OTHER PUBLICATIONS

Extended European Search Report dated Jun. 30, 2020 issued in corresponding EP Appln. No. 19200767.2.

(Continued)

*Primary Examiner* — Julianna N Harvey
(74) *Attorney, Agent, or Firm* — Carter, DeLuca & Farrell LLP

(57) ABSTRACT

A surgical access device includes a housing, a tubular member extending from the housing, a valve disposed on the housing, and a tip member at a distal end of the tubular member. The housing includes a seal and the tubular member includes a plurality of lumens extending therethrough. The valve is fluidly coupled with a first lumen of the plurality of lumens and the tip member includes a first port that is aligned and fluidly coupled with the first lumen of the plurality of lumens. The first port is configured to direct a fluid towards a predetermined location.

10 Claims, 15 Drawing Sheets

(56) References Cited

U.S. PATENT DOCUMENTS

| | | | |
|---|---|---|---|
| 5,203,767 A | 4/1993 | Cloyd | |
| 5,207,213 A | 5/1993 | Auhll et al. | |
| 5,274,874 A | 1/1994 | Cercone et al. | |
| 5,313,934 A | 5/1994 | Wiita et al. | |
| 5,337,730 A | 8/1994 | Maguire | |
| 5,337,800 A | 8/1994 | Cook | |
| 5,354,302 A | 10/1994 | Ko | |
| 5,382,297 A | 1/1995 | Valentine et al. | |
| 5,392,766 A | 2/1995 | Masterson et al. | |
| 5,400,767 A | 3/1995 | Murdoch | |
| 5,505,707 A | 4/1996 | Manzie et al. | |
| 5,514,084 A | 5/1996 | Fisher | |
| 5,518,502 A | 5/1996 | Kaplan et al. | |
| 5,630,795 A | 5/1997 | Kuramoto et al. | |
| 5,735,792 A | 4/1998 | Vanden Hoek et al. | |
| 5,755,782 A | 5/1998 | Love et al. | |
| 5,842,971 A | 12/1998 | Yoon | |
| 5,931,833 A | 8/1999 | Silverstein | |
| 5,944,654 A | 8/1999 | Crawford | |
| 6,110,103 A * | 8/2000 | Donofrio | A61B 1/126 600/114 |
| 6,354,992 B1 | 3/2002 | Kato | |
| 6,387,044 B1 | 5/2002 | Tachibana et al. | |
| 6,551,270 B1 * | 4/2003 | Bimbo | A61B 17/3421 604/167.03 |
| 6,682,165 B2 | 1/2004 | Yearout | |
| 6,755,782 B2 | 6/2004 | Ogawa | |
| 6,923,759 B2 | 8/2005 | Kasahara et al. | |
| 7,300,445 B2 | 11/2007 | Adams | |
| 7,316,683 B2 | 1/2008 | Kasahara et al. | |
| 7,339,341 B2 | 3/2008 | Oleynikov et al. | |
| 7,530,984 B2 | 5/2009 | Sonnenschein et al. | |
| 7,596,828 B2 | 10/2009 | Evdokimo | |
| 7,922,701 B2 | 4/2011 | Buchman | |
| 7,959,561 B2 | 6/2011 | Akui et al. | |
| 8,915,842 B2 * | 12/2014 | Weisenburgh, II | A61B 1/00091 600/156 |
| 2002/0022762 A1 | 2/2002 | Beane et al. | |
| 2002/0065450 A1 | 5/2002 | Ogawa | |
| 2003/0073955 A1 | 4/2003 | Otawara | |
| 2006/0293559 A1 | 12/2006 | Grice et al. | |
| 2007/0149850 A1 | 6/2007 | Spivey et al. | |
| 2007/0208220 A1 | 9/2007 | Carter | |
| 2007/0208221 A1 | 9/2007 | Kennedy et al. | |
| 2007/0213667 A1 | 9/2007 | Prusmack | |
| 2007/0282253 A1 | 12/2007 | Sasaki | |
| 2007/0282356 A1 | 12/2007 | Sonnenschein et al. | |
| 2007/0293719 A1 | 12/2007 | Scopton et al. | |
| 2007/0299310 A1 | 12/2007 | Phillips | |
| 2008/0015618 A1 | 1/2008 | Sonnenschein et al. | |
| 2008/0058852 A1 | 3/2008 | Ihde | |
| 2008/0081948 A1 | 4/2008 | Weisenburgh et al. | |
| 2008/0188715 A1 | 8/2008 | Fujimoto | |
| 2008/0319266 A1 | 12/2008 | Poll et al. | |
| 2009/0005799 A1 | 1/2009 | Franer et al. | |
| 2009/0049627 A1 | 2/2009 | Kritzler | |
| 2009/0105543 A1 | 4/2009 | Miller et al. | |
| 2009/0112065 A1 | 4/2009 | Harrel | |
| 2009/0234193 A1 | 9/2009 | Weisenburgh, III et al. | |
| 2009/0240111 A1 | 9/2009 | Kessler et al. | |
| 2009/0264703 A1 | 10/2009 | Pribanic | |
| 2009/0270681 A1 | 10/2009 | Moreno et al. | |
| 2009/0270685 A1 | 10/2009 | Moreno et al. | |
| 2009/0270686 A1 | 10/2009 | Duke et al. | |
| 2009/0270813 A1 | 10/2009 | Moreno et al. | |
| 2009/0270817 A1 | 10/2009 | Moreno et al. | |
| 2009/0270818 A1 | 10/2009 | Duke | |
| 2009/0287052 A1 | 11/2009 | Amos et al. | |
| 2010/0022958 A1 | 1/2010 | Moreno, Jr. et al. | |
| 2010/0030031 A1 | 2/2010 | Goldfarb et al. | |
| 2010/0174144 A1 | 7/2010 | Hsu et al. | |
| 2010/0256453 A1 | 10/2010 | Hammond et al. | |
| 2011/0015491 A1 * | 1/2011 | Ravikumar | A61B 1/32 600/233 |
| 2011/0152776 A1 | 6/2011 | Hartoumbekis et al. | |
| 2011/0230716 A1 | 9/2011 | Fujimoto | |
| 2015/0265138 A1 * | 9/2015 | Poll | A61B 1/00119 600/123 |

FOREIGN PATENT DOCUMENTS

| | | |
|---|---|---|
| EP | 1210904 A2 | 6/2002 |
| EP | 1323373 A2 | 7/2003 |
| EP | 1911409 A1 | 4/2008 |
| EP | 2111782 A2 | 10/2009 |
| JP | 2005040184 A | 2/2005 |
| JP | 2005052229 A | 3/2005 |
| JP | 2007105314 A | 4/2007 |
| JP | 2007130167 A | 5/2007 |
| JP | 2008132282 A | 6/2008 |
| JP | 2008279202 A | 11/2008 |
| JP | 2010022758 A | 2/2010 |
| WO | 9824359 A1 | 6/1998 |
| WO | 2008153841 A2 | 12/2008 |
| WO | 2009018288 A1 | 2/2009 |

OTHER PUBLICATIONS

Partial European Search Report dated Jan. 14, 2020 issued in corresponding EP Appln. No. 19200767.2.

European Examination Report dated Jul. 1, 2021 issued in corresponding EP Appln. No. 19 200 767.2.

European Examination Report dated Jun. 2, 2022 issued in corresponding EP Appln. No. 19 200 767.2.

* cited by examiner

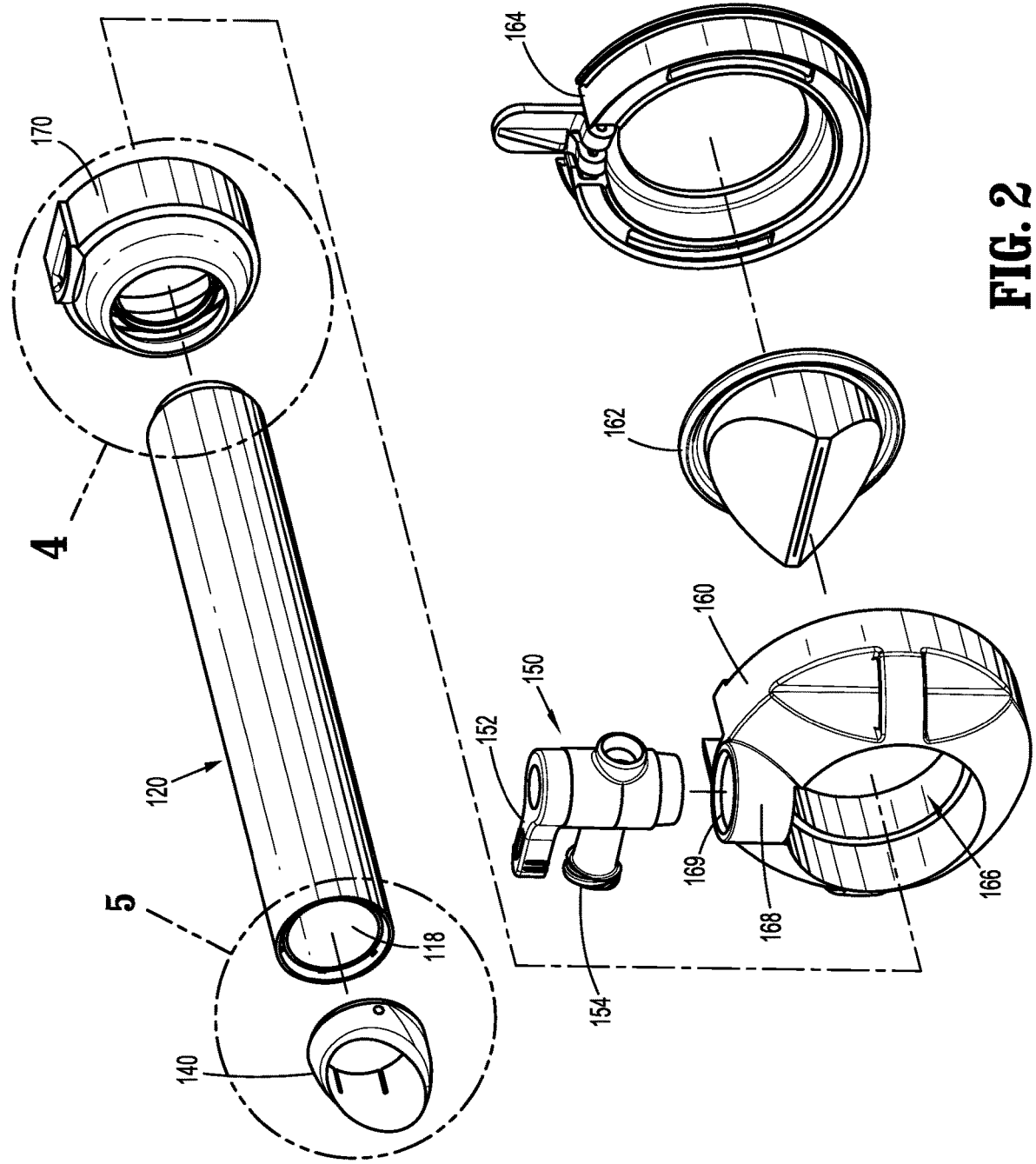

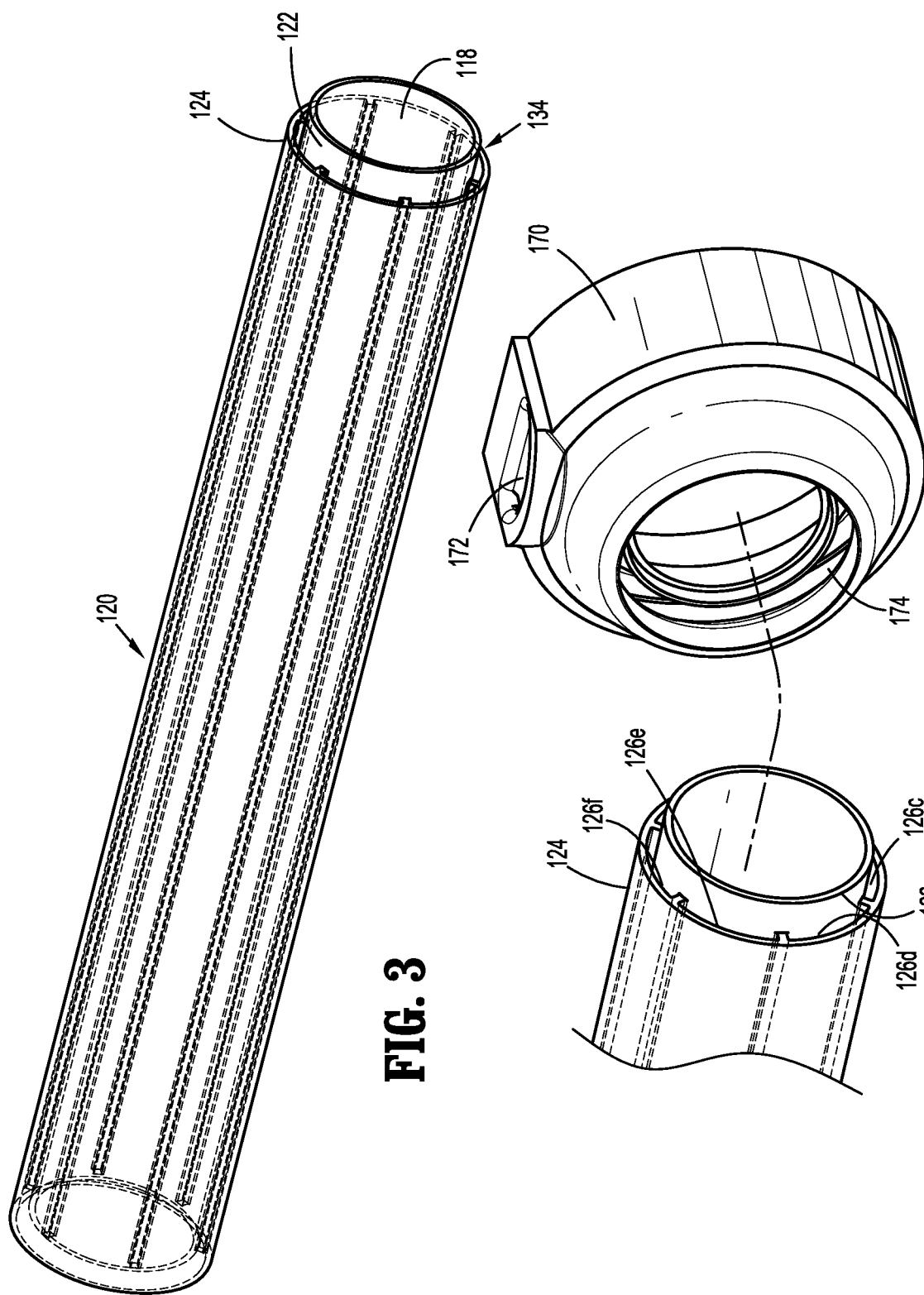

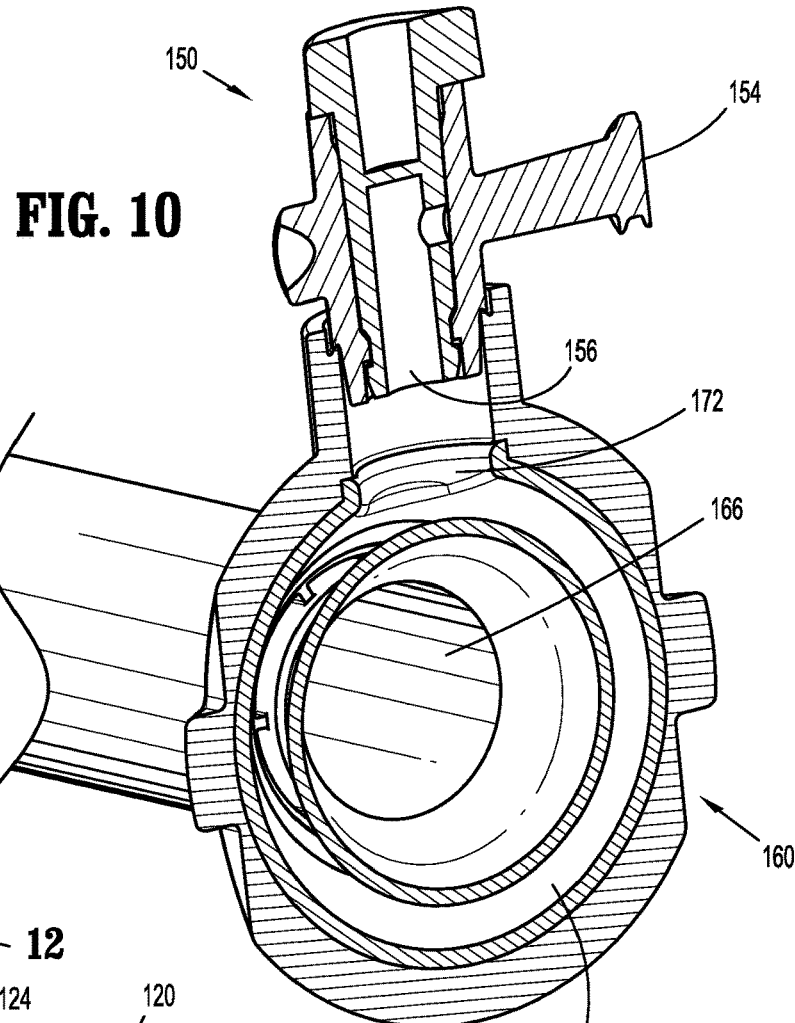
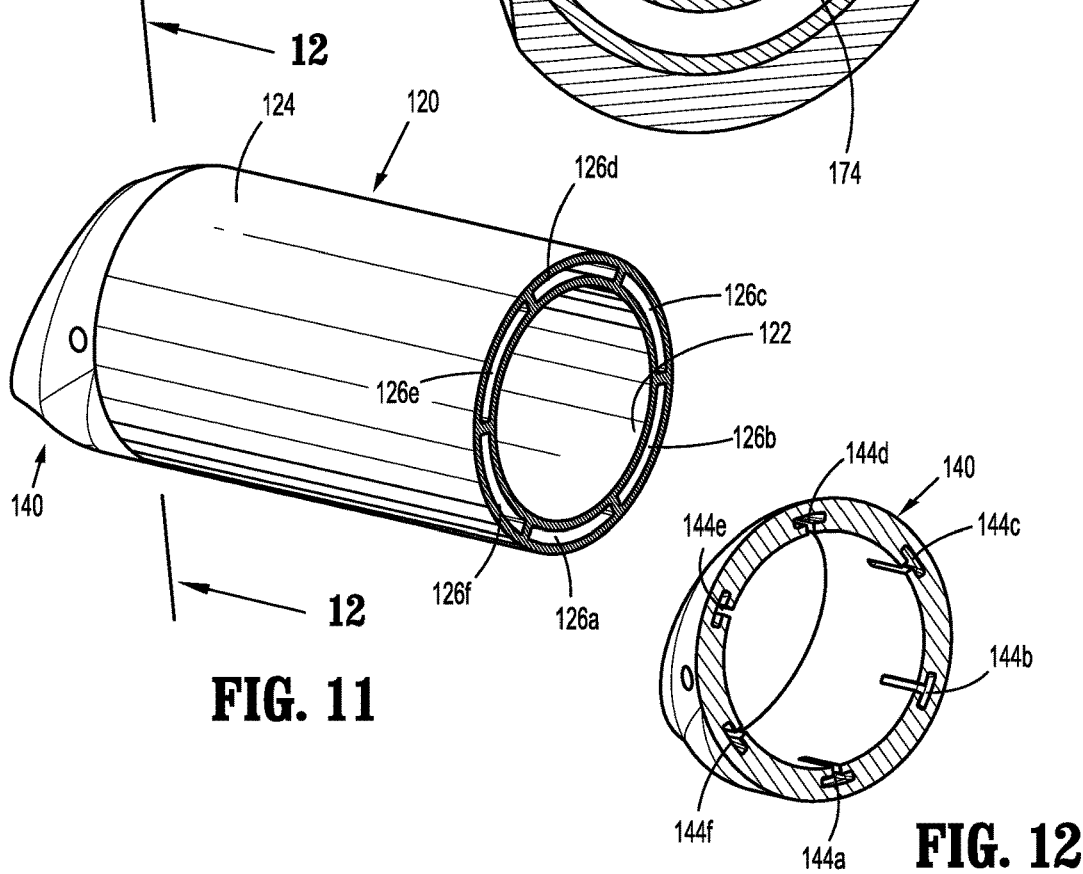

MULTI LUMEN ACCESS DEVICE

CROSS-REFERENCE TO RELATED APPLICATIONS

This application is a continuation-in-part of U.S. patent application Ser. No. 16/149,479, filed Oct. 2, 2018, the contents of which is hereby incorporated by reference in its entirety.

TECHNICAL FIELD

The present disclosure relates to a surgical access device. More particularly, the present disclosure relates to a surgical access device having multiple lumens.

BACKGROUND OF RELATED ART

Minimally invasive surgery has become increasingly popular in recent years. Minimally invasive surgery eliminates the need to cut a large incision in a patient, thereby reducing discomfort, recovery time, and many of the deleterious side effects associated with traditional open surgery. Minimally invasive viewing instruments (e.g., laparoscopes and endoscopes) are optical instruments to facilitate the viewing of internal tissues and/or organs.

Laparoscopic surgery involves the placement of a laparoscope in a small incision in the abdominal wall of a patient to view the surgical site. Endoscopic surgery involves the placement of an endoscope in a naturally occurring orifice (e.g., mouth, nose, anus, urethra, or vagina) to view the surgical site. Other minimally invasive surgical procedures include video assisted thoracic surgery and cardiovascular surgery conducted through small incisions between the ribs. These procedures also utilize scopes to view the surgical site.

A typical minimally invasive viewing instrument (e.g., a laparoscope or an endoscope) includes a housing, an elongated shaft extending from one end of the housing, and a lens that is provided in the distal end of the shaft. A camera viewfinder extends from the other end of the housing. A camera is connected to the housing and transmits images of the surgical field viewed through the lens to a monitor on which the images are displayed. During a surgical procedure, the distal end portion of the shaft is extended into the patient, while the proximal end portion of the shaft, the housing, and the camera viewfinder remain outside the patient. In this manner, the laparoscope/endoscope is positioned and adjusted to view particular anatomical structures in the surgical field on the monitor.

During insertion of an endoscope or a laparoscope into the body and during the surgical procedure, debris (e.g., organic matter and moisture) may be deposited on the lens of the endoscope. The buildup of debris and condensation on the lens impairs visualization of the surgical site, and often necessitates cleaning of the lens. This may require the surgeon to remove, clean, and re-insert the endoscope one or more times during a surgical procedure to maintain a clear image of the surgical site. Cleaning of the instruments often necessitates removal of the instruments from the surgical site, thereby increasing the time required to perform the surgical procedure.

Systems for cleaning viewing devices such as endoscopes and laparoscopes are known in the art. Examples of known systems and techniques are described in U.S. Patent Application Publication No. 2009/0234193 to Weisenburgh, II et al., U.S. Pat. No. 8,047,215 to Sasaki, and U.S. Pat. No. 8,888,689 to Poll et al.

SUMMARY

According to one embodiment of the present disclosure, a surgical access device includes a housing including a seal, a tubular member extending from the housing, the tubular member including a plurality of lumens extending therethrough, a valve disposed on the housing and fluidly coupled with a first lumen of the plurality of lumens, and a tip member disposed at a distal end of the tubular member, the tip member including a first port that is aligned and fluidly coupled with the first lumen of the plurality of lumens, the first port configured to direct a fluid towards a predetermined location.

The surgical access device may include the tubular member with an inner tube and an outer tube defining an annular chamber therebetween. The annular chamber may be fluidly coupled to the valve and the first lumen of the plurality of lumens is disposed within the annular chamber.

The surgical access device may include the annular chamber having the second lumen of the plurality of lumens extending therethrough. The second lumen of the plurality of lumens may be fluidly coupled to a second port located in the tip member. The second port may be configured to direct a fluid towards the predetermined location.

The surgical access device of may include the inner tubular member defining a third lumen of the plurality of lumens extending therethrough.

The surgical access device may include the first and second lumens of the plurality of lumens being radially spaced apart.

The surgical access device may include the predetermined location lying along a central longitudinal axis of the tubular member.

The surgical access device may include the valve fluidly coupling a source of fluid to the first and second lumens of the plurality of lumens.

The surgical access device may include the first port being offset from the second port by 180°.

The surgical access device may include each of the first and second ports having a spray pattern that covers 180° of the predetermined location.

The surgical access device may include the first port and the second port being radially offset in a range between about 60° and about 120°.

The surgical access device may include the channel being configured to receive a viewing instrument therethrough.

The surgical access device may be insertable through an opening in tissue.

According to an embodiment of the present disclosure, a method for cleaning a viewing instrument includes moving a lens of a viewing instrument towards a target area defined in a channel of a tubular member, the tubular member including an inner tube disposed in an outer tube defining an annular chamber therebetween, and dispensing a cleaning fluid from a first port towards the target area, the first port located on a tip member, the tip member located at a distal end of the tubular member, the first port fluidly coupled to a first lumen of a plurality of lumens that is disposed in the annular chamber, the first lumen of the plurality of lumens fluidly coupled to a valve for controlling flow of the cleaning fluid.

The method may include dispensing the cleaning fluid from a second port towards the target area. The second port may be located on the tip member and fluidly coupled to a second lumen of the plurality of lumens that is disposed in the annular chamber. The second lumen of the plurality of lumens may be fluidly coupled to the valve for controlling flow of the cleaning fluid.

The method may include moving the optical portion into a third lumen of the plurality of lumens defined by the inner tube.

The method may further include positioning the tubular member through tissue of a patient. The tubular member may extend from a housing with a seal member.

The method may further include repositioning the lens of the viewing instrument along a longitudinal axis of the tubular member such that the lens moves into and out of the predetermined region.

The method may further include viewing an image on a monitor coupled to the viewing instrument during repositioning of the lens.

According to an embodiment of the present disclosure a surgical access device includes a housing with a seal, a tubular member extends from the housing with lumens extending therethrough, a valve disposed on the housing that is fluidly coupled with the lumens, and a tip member disposed at a distal end of the tubular member, the tip member including a first port aligned and fluidly coupled with one of the lumens, the first port including a cavity having a tapered configuration extending between a proximal region and a distal region, the proximal region having a first width and the distal region having a second width less than the first width.

The surgical access device may include a second port with a pocket extending between proximal and distal regions thereof, the pocket having a uniform width.

The surgical access device may have a velocity of a fluid exiting the first port greater than a velocity of a fluid exiting the second port.

The surgical access device may include a first duct of the first port that has a length equal to a length of a second duct of the second port.

The surgical access device may have an increased velocity of a fluid passing from the proximal region of the first port to the distal region of the first port as a result of the tapered configuration of the cavity.

The surgical access device may include the tubular member having an inner tube and an outer tube that define an annular chamber therebetween. The annular chamber may be fluidly coupled to the valve. The lumens may be disposed within the annular chamber and radially spaced apart.

The surgical access device may include the first port being offset from the second port by 180°.

The surgical access device may include the first port and the second port being radially offset in a range between about 60° and about 120°.

The surgical access device may include a third port, the third port having a cavity with a tapered configuration comparable to the tapered configuration of the first port.

The surgical access device may include a channel extending through the tubular member, the channel configured to receive a viewing instrument therethrough.

The surgical access device may include a central longitudinal axis defined through the tubular member, the first port is spaced a first distance from the central longitudinal axis of the tubular member and the third port is spaced a third distance from the central longitudinal axis of the tubular member. The first distance may be different from the third distance.

The surgical access device may include a portion of the distal region of the first port being angled towards the central longitudinal axis of the tubular member such that fluid flow through the first port is directed towards the central longitudinal axis of the tubular member.

The surgical access device may include a supply of insufflation fluid coupled to a first inlet of a multi-way valve and a supply of cleaning fluid coupled to a second inlet of the multi-way valve. An outlet of the multi-way valve may be fluidly coupled to an inlet of the valve disposed on the housing of the surgical access device.

The surgical access device may include the supply of cleaning fluid having a bulb. Actuating the bulb may deliver a quantity of cleaning fluid to the second inlet of the multi-way valve.

The surgical access device may include the multi-way valve having a button that is transitionable between a first position that couples the second inlet port to the outlet port and a second position that couples the first inlet port to the outlet port.

BRIEF DESCRIPTION OF THE DRAWINGS

Various embodiments of the present disclosure are illustrated herein with reference to the accompanying drawings, wherein:

FIG. 2 is an exploded, perspective view of the surgical access device of FIG. 1 with parts separated;

FIG. 3 is a perspective view of a tubular member of the surgical access device of FIG. 1 shown in phantom;

FIG. 4 is an enlarged view of the indicated area of detail of FIG. 2;

FIG. 10 is an end, cross-sectional view of the surgical access device of FIG. 7 taken along section line 10-10 in FIG. 7;

FIG. 11 is a cross-sectional view of the surgical access device of FIG. 7 taken along section line 11-11 in FIG. 7;

FIG. 12 is an end cross-sectional view of the distal tip of the surgical access device of FIG. 11 taken along section line 12-12 in FIG. 11;

DETAILED DESCRIPTION

Figure 1:
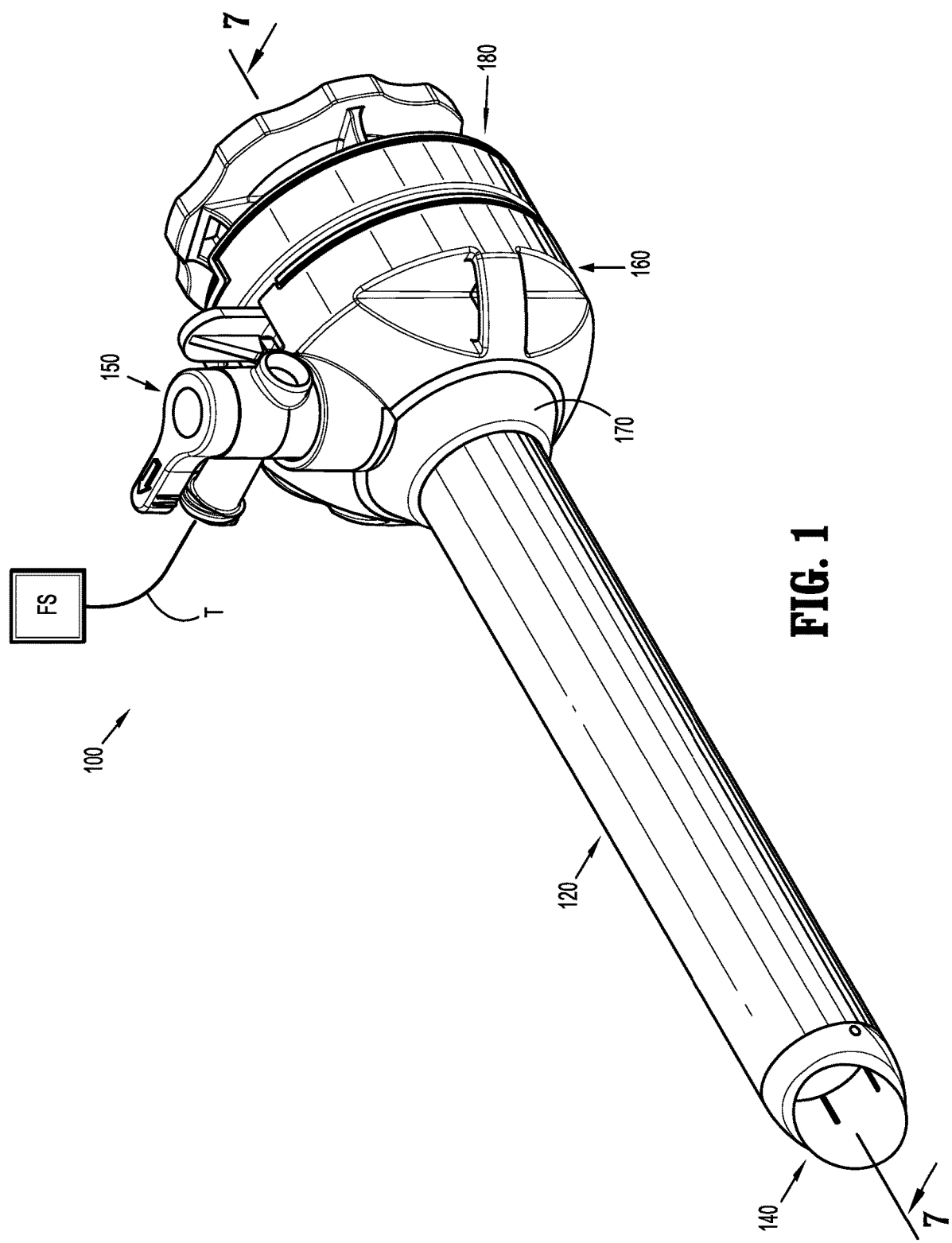
FIG. 1 is a perspective view of a surgical access device coupled to a source of fluid according to an embodiment of the present disclosure.

Embodiments of the presently disclosed surgical access device are described in detail with reference to the drawings, wherein like reference numerals designate corresponding elements in each of the several views. As used herein, the term "distal" refers to that portion of the instrument, or component thereof which is farther from the user while the term "proximal" refers to that portion of the instrument or component thereof which is closer to the user.

Various embodiments of a surgical access device are described herein. With initial reference to FIGS. 1 and 2, a surgical access device 100 is illustrated. The components of the surgical access device 100 may be formed from suitable biocompatible materials such as medical grade metals (e.g., stainless steel), polymeric materials (e.g., polycarbonate), or combinations thereof. The surgical access device 100 includes a housing 160. A collar 170 is insertable through the housing 160 and a tubular member 120 extends from a distal end of the collar 170. A tip member 140 is located at a distal end of the tubular member 120. A seal assembly 180 is releasably coupled to a proximal end of the housing 160. An example of a suitable seal assembly usable with the presently disclosed surgical access device 100 is described in U.S. Pat. No. 10,022,149, issued on Jul. 17, 2018, the entire contents of which are hereby incorporated by reference. It is contemplated that the tubular member 120 may include a plurality of spaced annular ribs along a portion of a length of the tubular member to improve retention of the surgical access device 100 in an opening through body tissue. An example of a cannula with annular ribs is disclosed in U.S. Pat. No. 8,740,925, issued on Jun. 3, 2014, the entire contents of which are hereby incorporated by reference. Additionally, the surgical access device 100 may include a fixation device such as a balloon, an umbrella, a foam collar, etc. An example of a surgical access device with a foam collar and an anchoring balloon is disclosed in U.S. Pat. No. 7,963,975, issued on Jun. 21, 2011, the entire contents of which are hereby incorporated by reference. The surgical access device 100 may include a combination of ribs, balloons, foam collars, or other known structures for securing an access device in body tissue.

Figure 7:
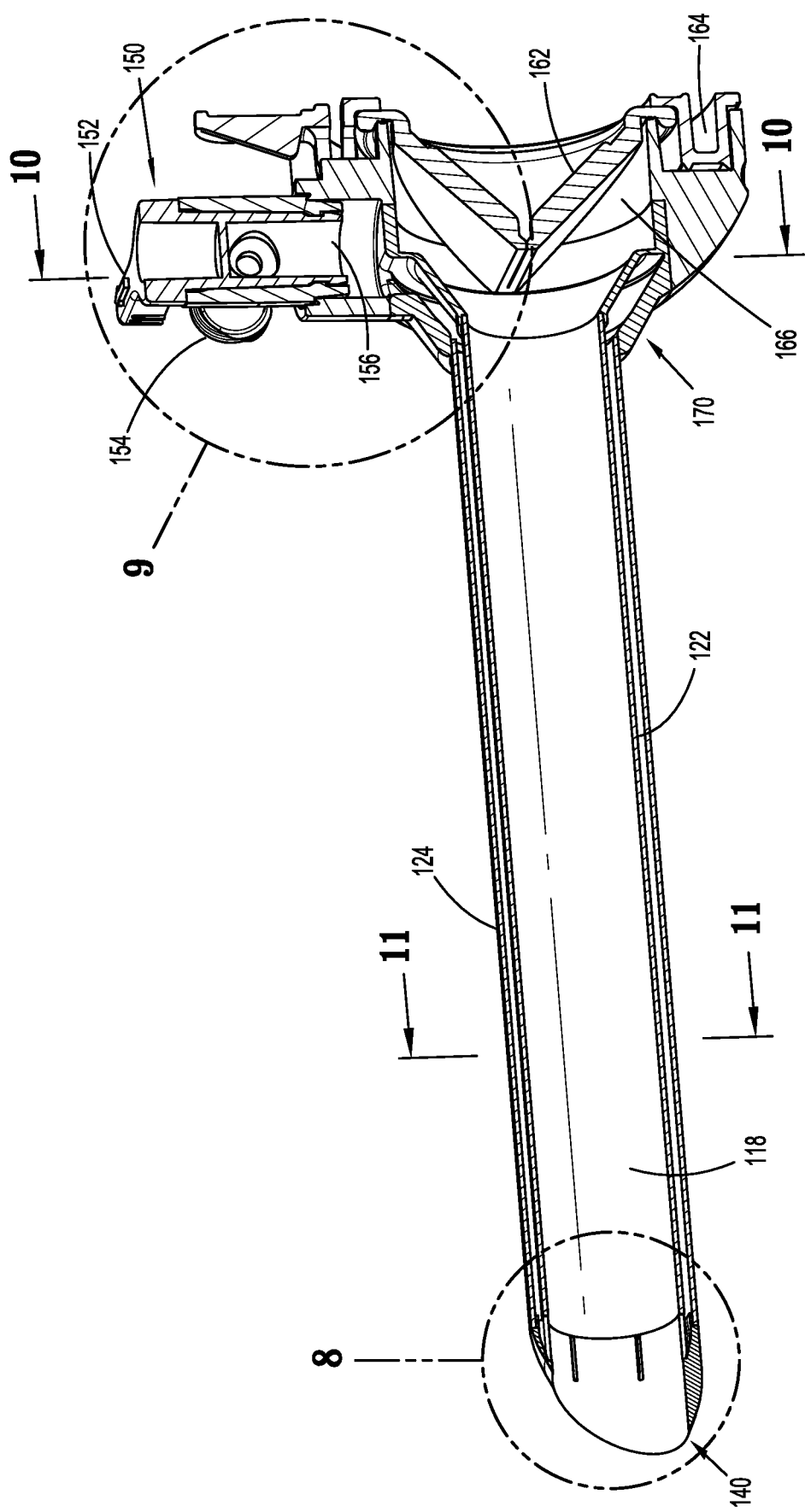
FIG. 7 is a side cross-sectional view of the surgical access device of FIG. 1 taken along section line 7-7 in FIG. 1.

The housing 160 has open proximal and distal ends defining a cavity 166 therein. The proximal opening has a larger diameter than the distal opening. A duck bill or zero-closure seal 162 is positioned in the cavity 166 of the housing 160 (FIG. 7). The zero-closure seal 162 is formed from a suitable resilient material (e.g., silicone) and is configured to prevent fluids from exiting proximally through the housing 160 in the absence of a surgical instrument (e.g., an endoscope) inserted therethrough. The zero-closure seal 162 is sandwiched between the housing 160 and a proximally positioned cap 164. The cap 164 is attached to the housing 160 to retain the zero-closure seal 162 in position and provide a fluid-tight boundary for the housing 160. The cap 164 may be attached to the housing 160 using ultrasonic or RF welding, adhesives, or any other suitable technique for the materials involved. The housing 160 further includes a port 168 having an opening 169 therethrough with a valve 150 positioned therein. The valve 150 has a lever 152 that is rotatable about an axis of the valve 150 allowing the user to open and close the valve 150. The lever 152 is rotatable between an open position of the valve 150 and a closed position of the valve 150. The lever 152 may be positioned in one of a plurality of intermediate positions allowing the user to adjust the flow rate of a fluid through the valve 150. With additional reference to FIGS. 4, 7, and 10, the valve 150 is fluidly coupled to an annular conduit 174 in the collar 170. In particular, the valve 150 is positioned in the opening 169 of port 168 and is aligned with an orifice 172 of the collar 170. This alignment allows fluid to flow through the valve 150, the orifice 172, and into the annular conduit 174. In turn, the annular conduit 174 is open at the proximal end of the collar 170 for fluidly coupling with lumens 126a-f in the tubular member 120 (FIGS. 7 and 10) as will be described in detail hereinbelow.

Referring now to FIGS. 1-4, 7, and 11, the tubular member 120 extends distally from the collar 170 and is formed of a suitable biocompatible material. The tubular member 120 is attached to the collar 170 using known techniques such as RF welding, ultrasonic welding, adhesives, etc. The tubular member 120 may be partially or completely transparent, translucent, or opaque. A passage or channel 118 extends between open proximal and distal ends of the tubular member 120. As illustrated, the tubular member 120 has substantially uniform inner and outer diameters. It is contemplated that either the inner diameter or the outer diameter may vary along a length of the tubular member 120 such that the tubular member 120 is tapered with one of the proximal or distal ends having different diameters from the other of the proximal or distal ends. It is further contemplated that the outer diameter of the tubular member 120 may be tapered such that the distal end has a smaller outer diameter than the proximal end while the inner diameter of the tubular member 120 does not vary along the length of the tubular member 120.

Further, the tubular member 120 has lumens 126a-f defined between an inner wall 122 of the tubular member 120 and an outer wall 124 of the tubular member 120. Each lumen 126 extends longitudinally along a length of the tubular member 120. The inner and outer walls 122, 124 have substantially the same length, but are axially staggered such that a recess 132 is defined in the distal region of the tubular member 120 (FIG. 5) and an extension 134 is defined in the proximal region of the tubular member 120 (FIG. 4). The number of lumens 126 disposed between the inner and outer walls 122, 124 of the tubular member 120 may vary. In embodiments, there may be as few as one or two lumens 126 and in other embodiments, there may be as many as six lumens 126 as illustrated in FIG. 3. However, this does not preclude a greater number of lumens 126 being defined between the inner and outer walls 122, 124 of the tubular member 120.

Each lumen 126 is fluidly coupled to the annular conduit 174 of the collar 170 such that fluid may be supplied to the lumens from a source of fluid FS (FIG. 1) that is coupled to the valve 150 using tubing T. The outlet 156 of the valve 150 is fluidly coupled to the annular conduit 174 via the orifice 172. The fluid may be a cleaning fluid including, but not limited to, an insufflation fluid (e.g., $CO_2$), sterile saline, a surfactant solution, etc. The fluid flow may be through the valve 150 towards the lumens 126a-f or through the valve 150 towards the source of fluid FS as determined by the differential pressure between the lumens 126a-f and an inlet 154 of the valve 150.

Figure 5:
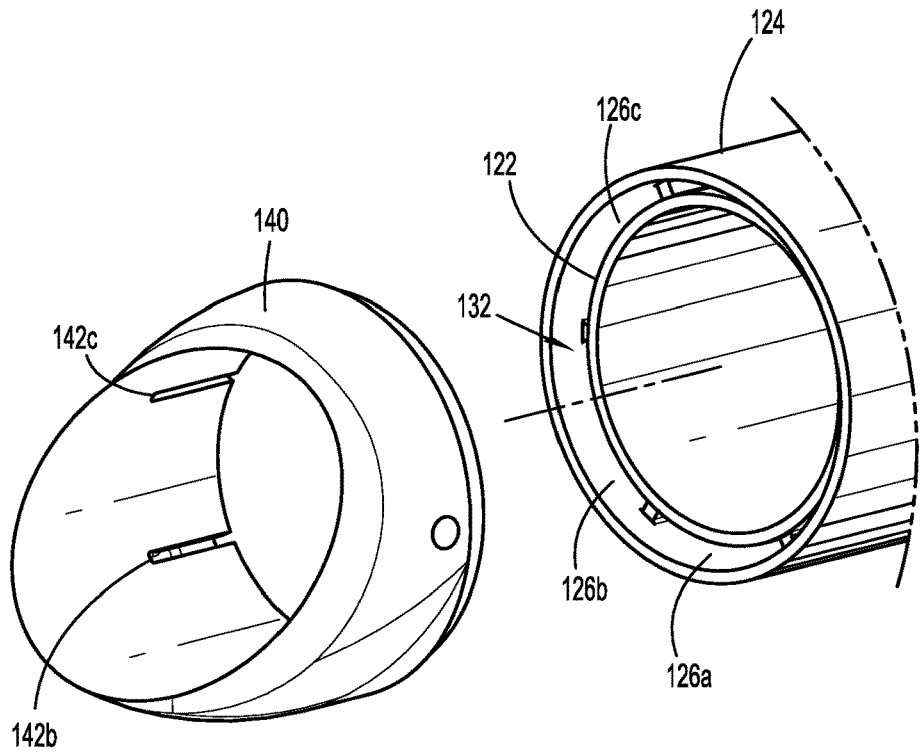
FIG. 5 is an enlarged view of the indicated area of detail of FIG. 2.
Figure 6:
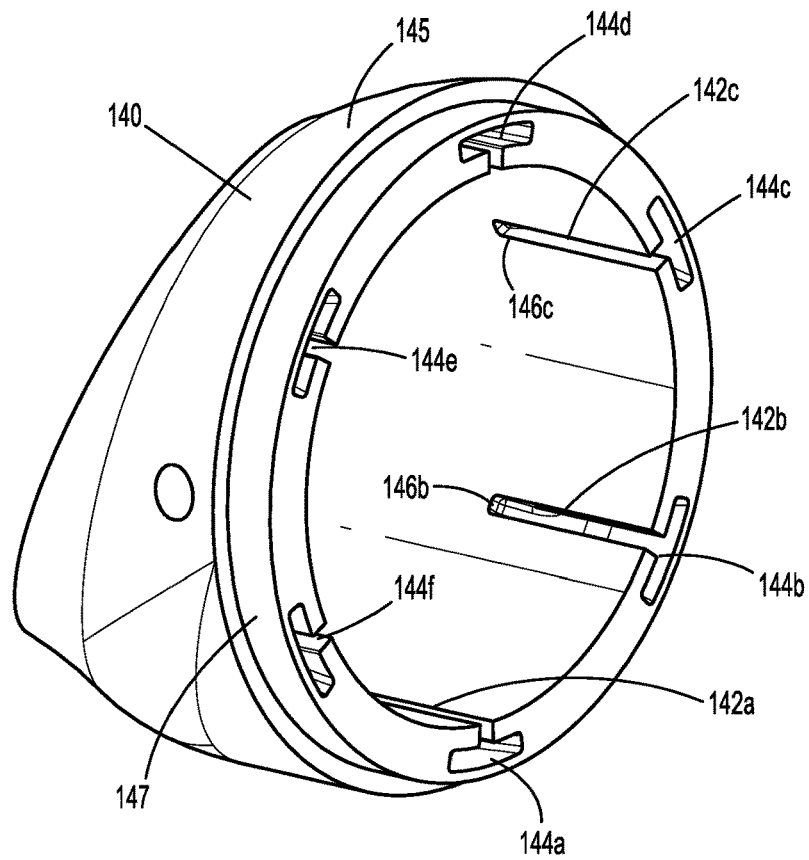
FIG. 6 is a perspective view of a distal tip of the surgical access device of FIG. 1.
Figure 8:
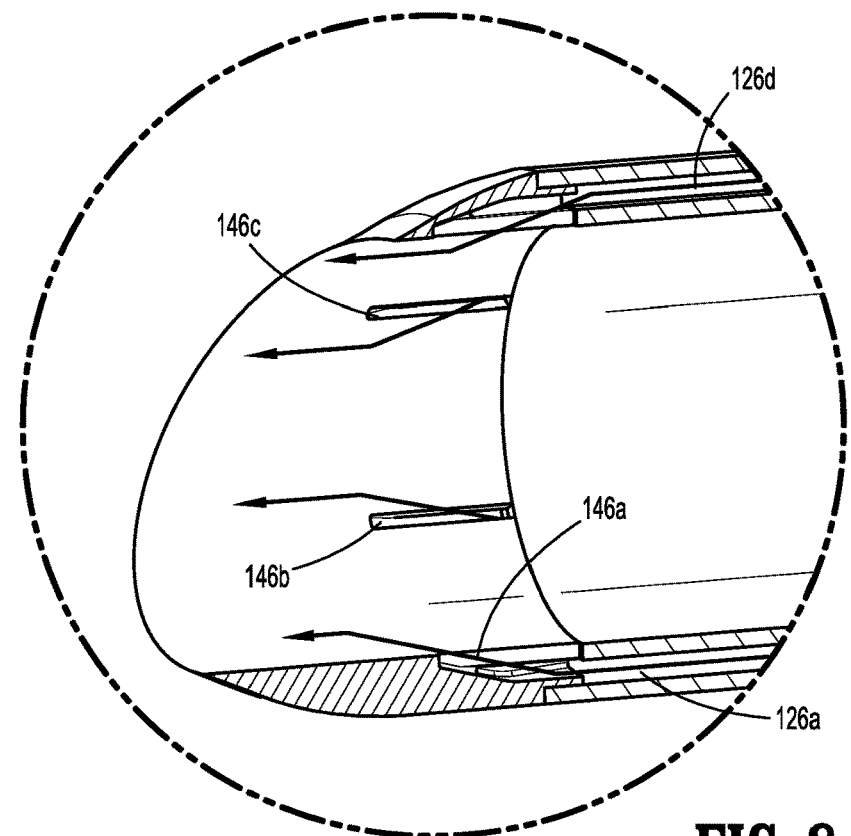
FIG. 8 is an enlarged view of the indicated area of detail of FIG. 7.
Figure 9:
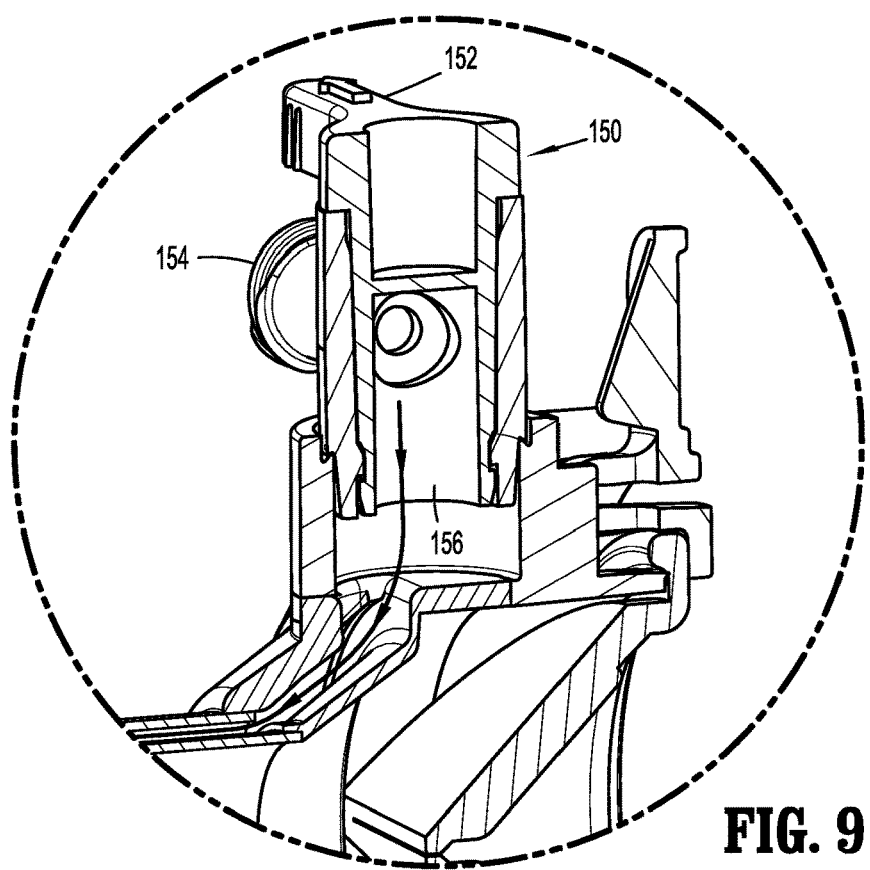
FIG. 9 is an enlarged view of the indicated area of detail of FIG. 7.

The tip member 140 is located at the distal end of the tubular member 120. With additional reference to FIGS. 5, 6, and 12, the tip member 140 includes a number of ports 142a-f equal to the number of lumens 126a-f of the tubular member 120. Each port 142 includes a duct 144 that is fluidly coupled to a corresponding lumen 126 of the tubular member 120. Each duct 144 extends longitudinally through the tip member 140 and fluidly couples one of the lumens 126 with an outlet 146 of the port 142. Each outlet 146 is configured to direct fluid to a predetermined or target region in the tip member 140 such that the output from each port 142 is directed to the same predetermined region resulting in an increase in the volume of fluid in the predetermined region. One or more of the outlets 146 may be configured to generate turbulent fluid flow. As shown in FIG. 8, a surface of the duct 144 of each port 142 is angled with respect to a longitudinal axis of the tubular member 120 which functions to direct the fluid from the duct 144 to the outlet 146 of the port 142 towards the predetermined region. The tip member 140 has a proximally extending portion 147 with an outer diameter is less than an outer diameter of a body 145 of tip member 140 and the proximally extending portion 147 is receivable in the recess 132 of the tubular member 120 (FIGS. 5 and 6). A distal portion of the tip member 140 is angled such that one location extends further distally than another location (FIG. 5). The tip member 140 is attached to the tubular member 120 using known techniques such as RF welding, ultrasonic welding, adhesives, etc. It is envisioned that one lumen 126 may be fluidly coupled to a plurality of ports 142. In one non-limiting example, the tubular member 120 may include three lumens 126a-c that are fluidly coupled to six ports 142a-f where each lumen 126 is coupled to two ports 142. Other combinations of lumens 126 and ports 142 are also possible.

In the illustrated embodiment with six ports, each port 142 is radially offset by 60° from the adjacent ports 142. In instances where greater or fewer than six ports are disposed in the tip member 140, the amount of radial offset of each port 142 from an adjacent port 142 may be defined by dividing 360° by the number of ports 142 in the distal tip (e.g., four ports would be radially offset by 90° and three ports would be radially offset by 120°). It is contemplated that the radial offset between ports 142 may not be uniform to create a different spray pattern of fluid (e.g., four ports that are radially offset by 30°).

Figure 6A:
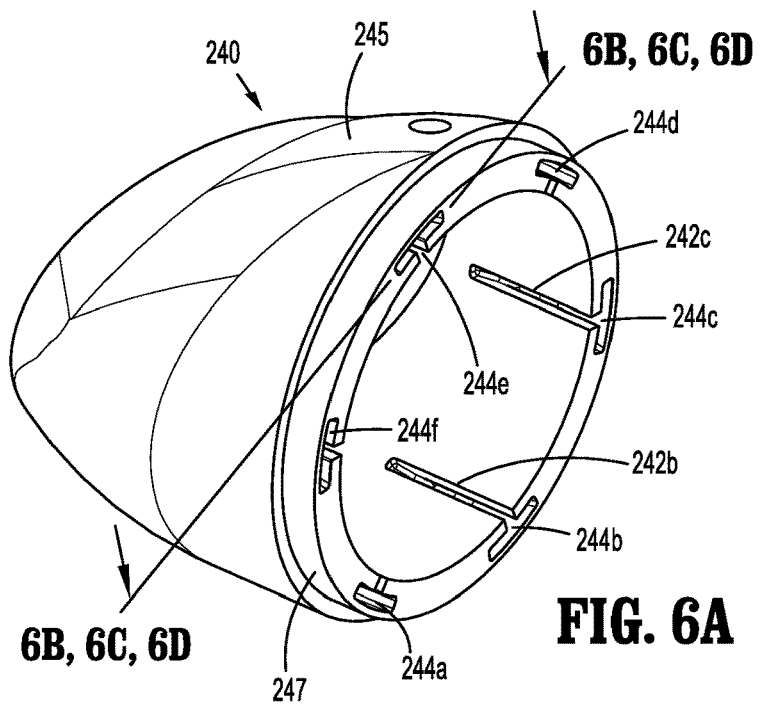
FIG. 6A is a rear perspective view of an alternate embodiment of a distal tip of the surgical access device of FIG. 1.
Figure 6B:
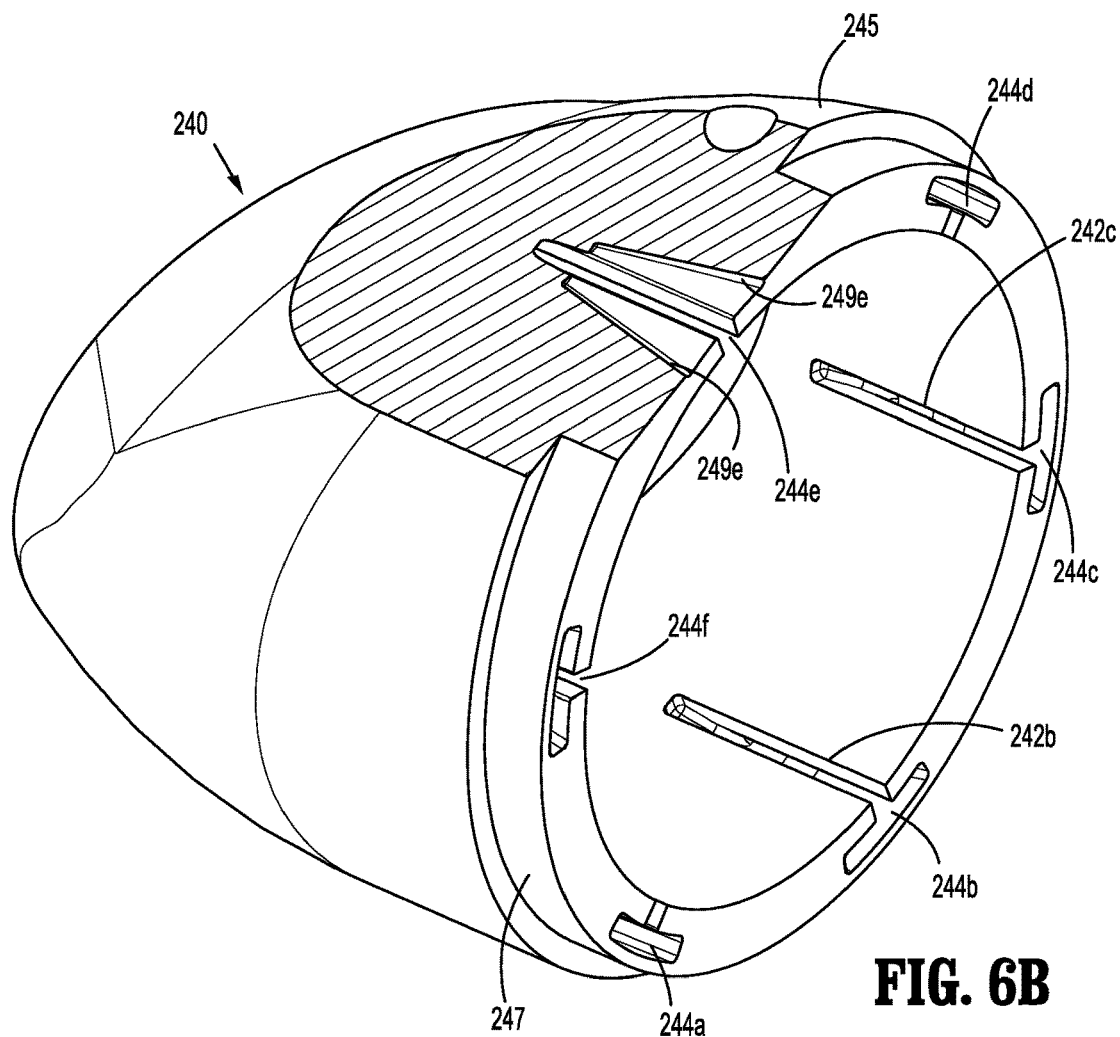
FIG. 6B is a perspective, partial cut-away view of the distal tip of FIG. 6A taken along section line 6B-6B of FIG. 6A.
Figure 6C:
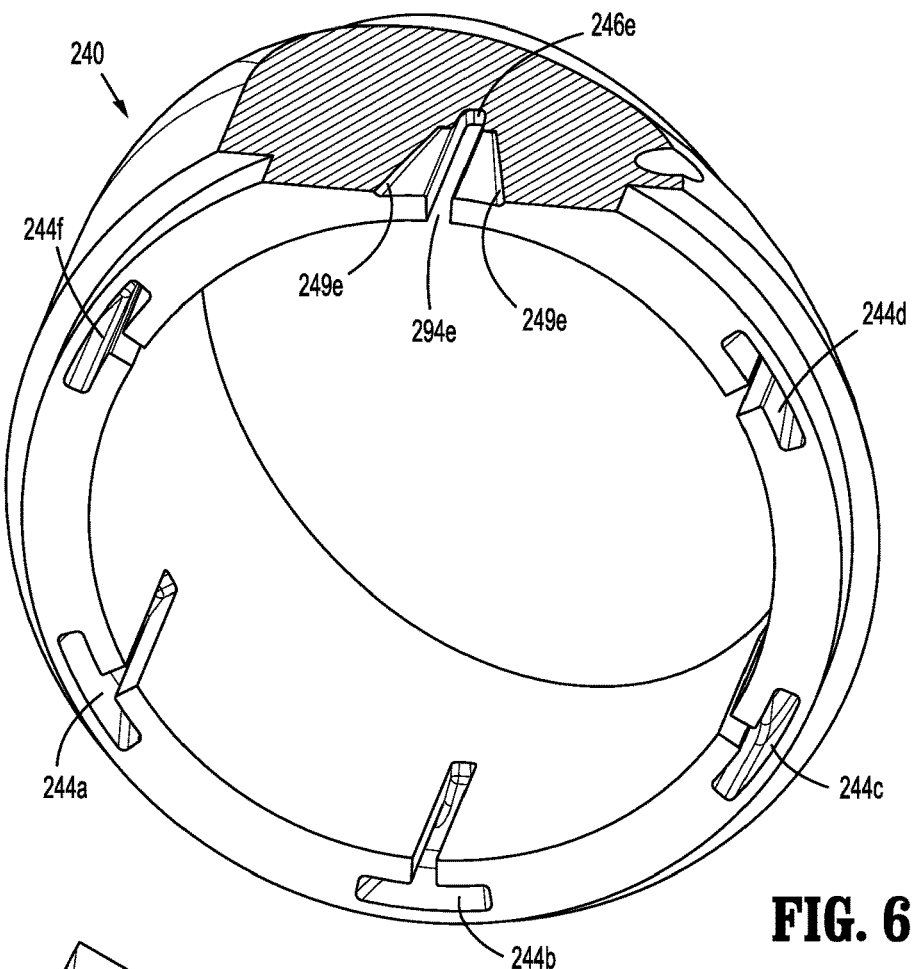
FIG. 6C is a rear perspective, partial cut-away view of the distal tip of FIG. 6A taken along section line 6C-6C of FIG. 6A.
Figure 6D:
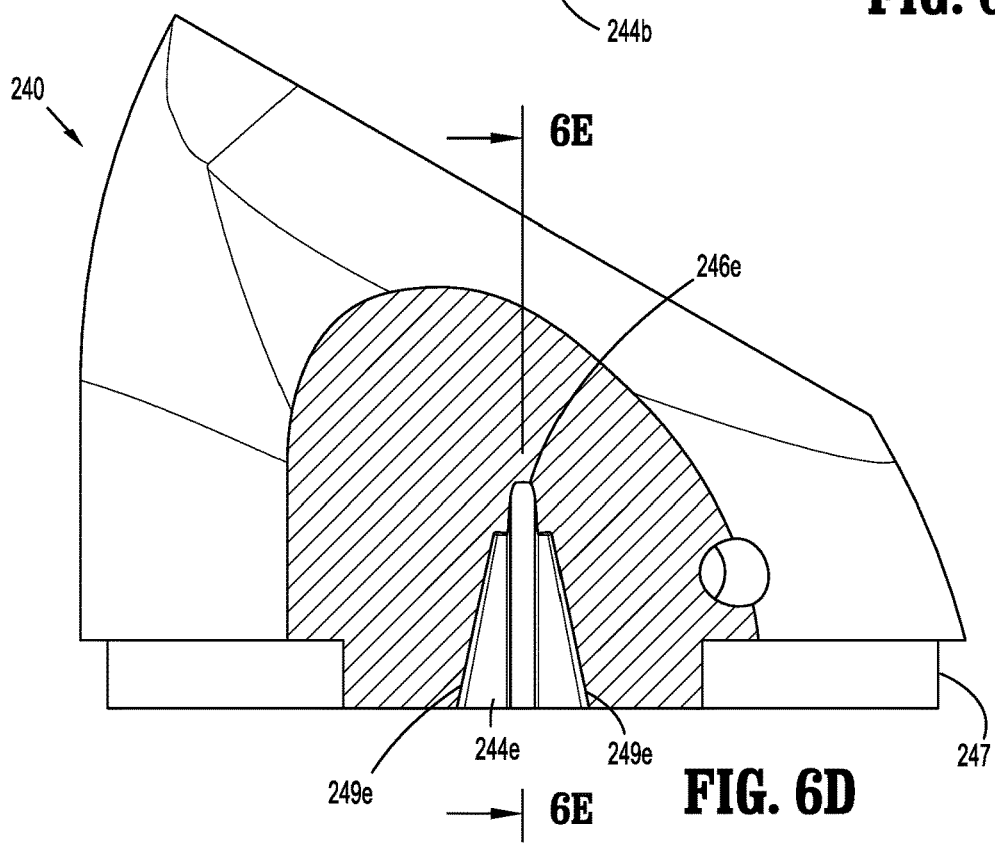
FIG. 6D is a top plan, partial cut-away view of the distal tip of FIG. 6A taken along section line 6D-6D of FIG. 6A.
Figure 6E:
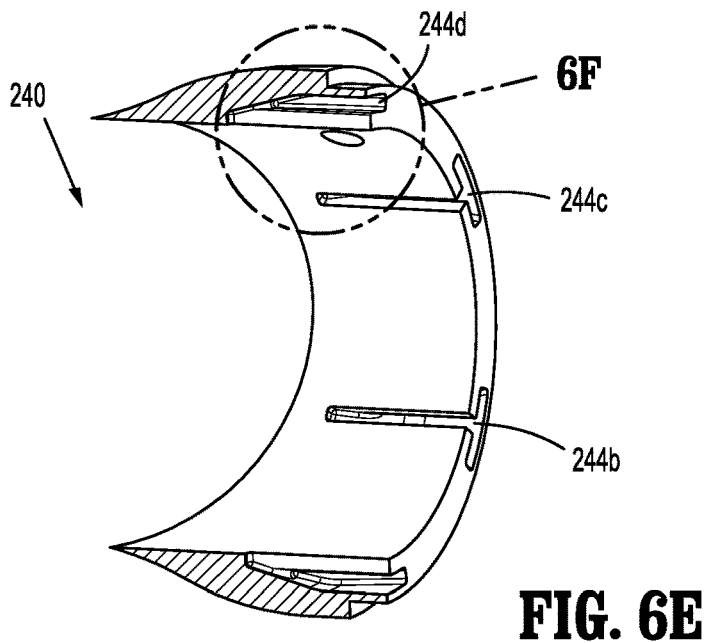
FIG. 6E is a side cross-sectional view of the distal tip of FIG. 6A taken along section line 6E-6E of FIG. 6D.
Figure 6F:
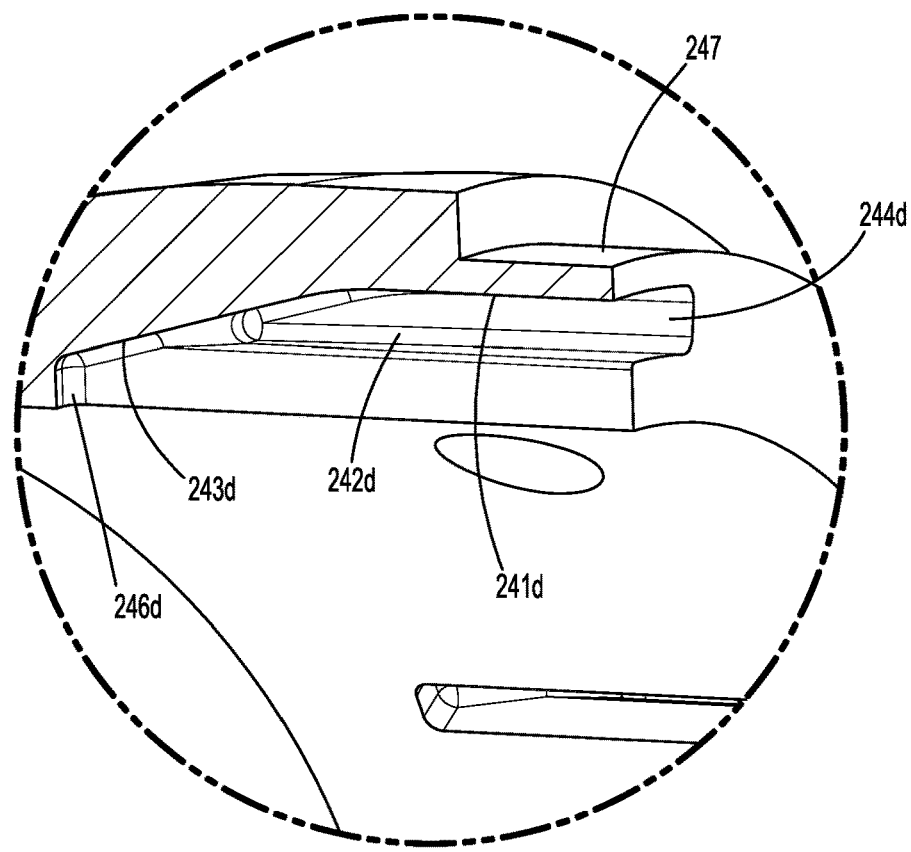
FIG. 6F is an enlarged view of the indicated area of detail of FIG. 6E.

An alternate embodiment of a tip member is illustrated in FIGS. 6A-6F and identified as tip member 240. Tip member 240 may be substituted for tip member 140 and positioned at the distal end of the tubular member 120. Tip member 240 has a proximally extending portion 247 with an outer diameter is less than an outer diameter of a body 245 of tip member 240 and the proximally extending portion 247 is receivable in the recess 132 of the tubular member 120 (FIG. 5). A distal portion of the tip member 240 is angled such that one location extends further distally than another location (FIG. 6D). The tip member 240 is attached to the tubular member 120 using known techniques such as RF welding, ultrasonic welding, adhesives, etc. Similar to tip member 140, tip member 240 includes a number of ports 242a-f equal to the number of lumens 126a-f of the tubular member 120. In the illustrated embodiment, there are six ports and six lumens. In other embodiments, the number of ports and lumens may be lesser or greater than six. Further still, other embodiments may include multiple ports fluidly coupled to a single lumen. In one non-limiting example, each lumen may be coupled to two or more ports. Further, it is contemplated that one lumen may be fluidly coupled to two ports, a second lumen may be fluidly coupled to a single port, and a third lumen may be fluidly coupled to three ports. Various combinations are also within the scope of the present disclosure. Each port 242 includes a duct 244 that is fluidly coupled to a corresponding lumen 126 of the tubular member 120. Each duct 244 extends longitudinally through the tip member 240 and fluidly couples one of the lumens 126 with an outlet 246 of the port 242. Each outlet 246 is configured to direct fluid to a predetermined or target region in the tip member 240 such that the output from each port 242 is directed to the same predetermined region resulting in an increase in the volume of fluid in the predetermined region. One or more of the outlets 246 may be configured to generate turbulent fluid flow. As illustrated in FIGS. 6E and 6F, the duct 244 of each port includes a floor 241 that extends along and parallel with a longitudinal axis "X" (FIG. 3) of the tubular member 120 and a face 243 that tapers towards a radial center of the tip member 240. The face 243 defines an angle with respect to a central longitudinal axis "Y" (FIG. 6G) of the tip member 240. This arrangement directs the fluid (i.e., insufflation or cleaning) from the duct 244 to the outlet 246 of the port 242 and towards a predetermined region of the tip member 240. When attached to the tubular member 120, the central longitudinal axis "Y" of the tip member 240 is aligned with the central longitudinal axis "X" of the tubular member 120. This is substantially similar to the configuration of each of ports 142a-f as seen in FIGS. 6 and 8.

In the illustrated embodiment with six ports, each port 242 is radially offset by 60° from the adjacent ports 242. In instances where greater or fewer than six ports are disposed in the tip member 240, the amount of radial offset of each port 242 from an adjacent port 242 may be defined by dividing 360° by the number of ports 242 in the distal tip (e.g., four ports would be radially offset by 90° and three ports would be radially offset by 120°). It is contemplated that the radial offset between ports 242 may not be uniform to create a different spray pattern of fluid (e.g., four ports that are radially offset by 30°).

Referring now to FIGS. 6B-6D, in addition to the floor 241 and the face 243, each port 242 further includes opposing sidewalls 249 that are angled with respect to a central longitudinal axis of the port 242 such that a distance between opposing sidewalls 249 in a proximal region of the port 242 is greater than a distance between opposing sidewalls 249 in a distal region of the port 242. The tapered arrangement of opposing sidewalls 249 accelerates the fluid passing through the port 242. When the area is reduced as the opposing sidewalls 249 taper towards each other, the pressure decreases resulting in an increase in fluid velocity. Increasing the velocity of the insufflation fluid or cleaning fluid aids in removing debris on a viewing element or lens of a minimally invasive viewing instrument when the viewing element is positioned in the stream of the insufflation or cleaning fluid. Additionally, the increased velocity helps minimize accumulation of debris on the viewing element when the viewing element is positioned in the stream of the insufflation or cleaning fluid.

Figure 6G:
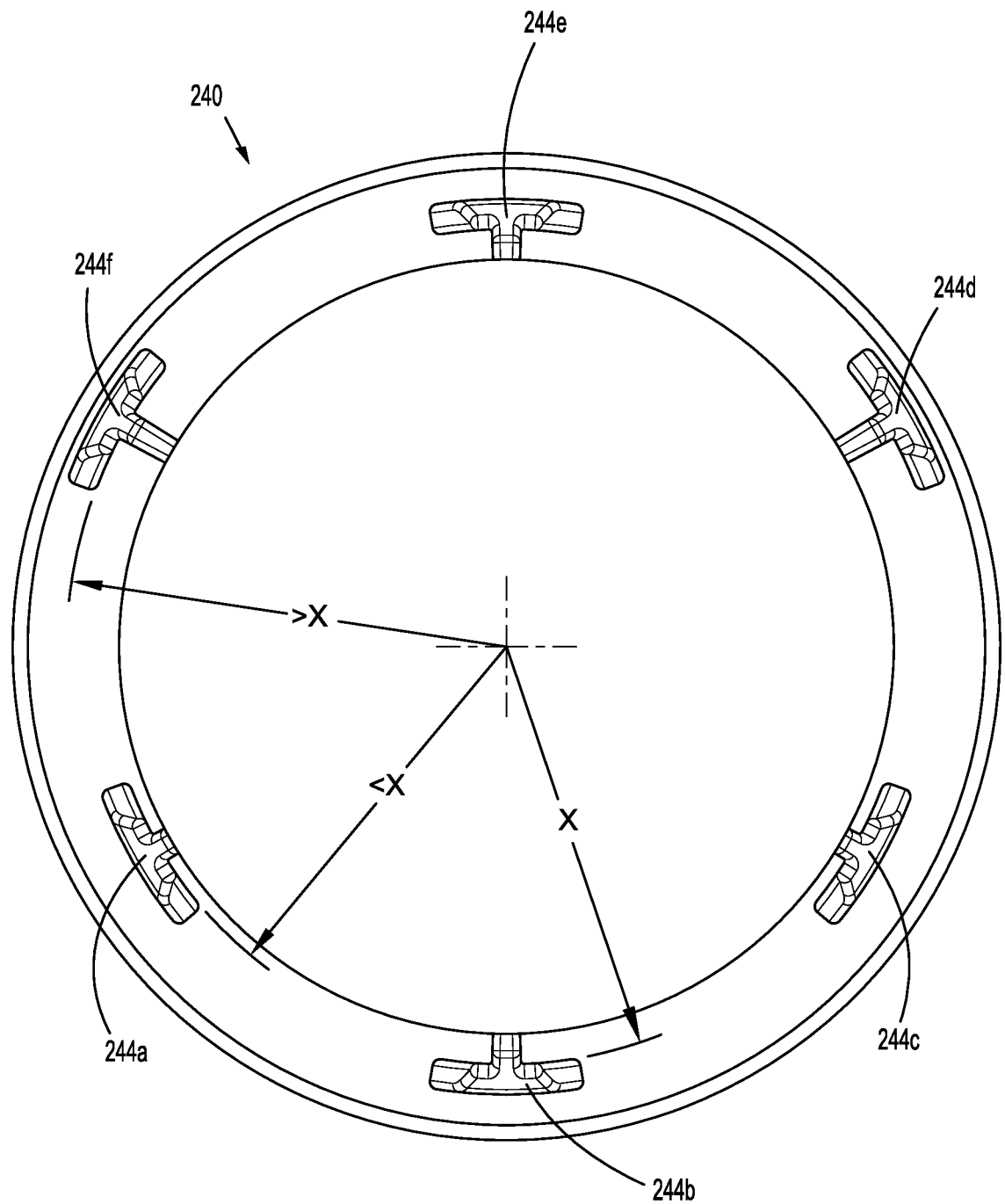
FIG. 6G is a rear view of a further embodiment of a distal tip of the surgical access device of FIG. 1.
Figure 6H:
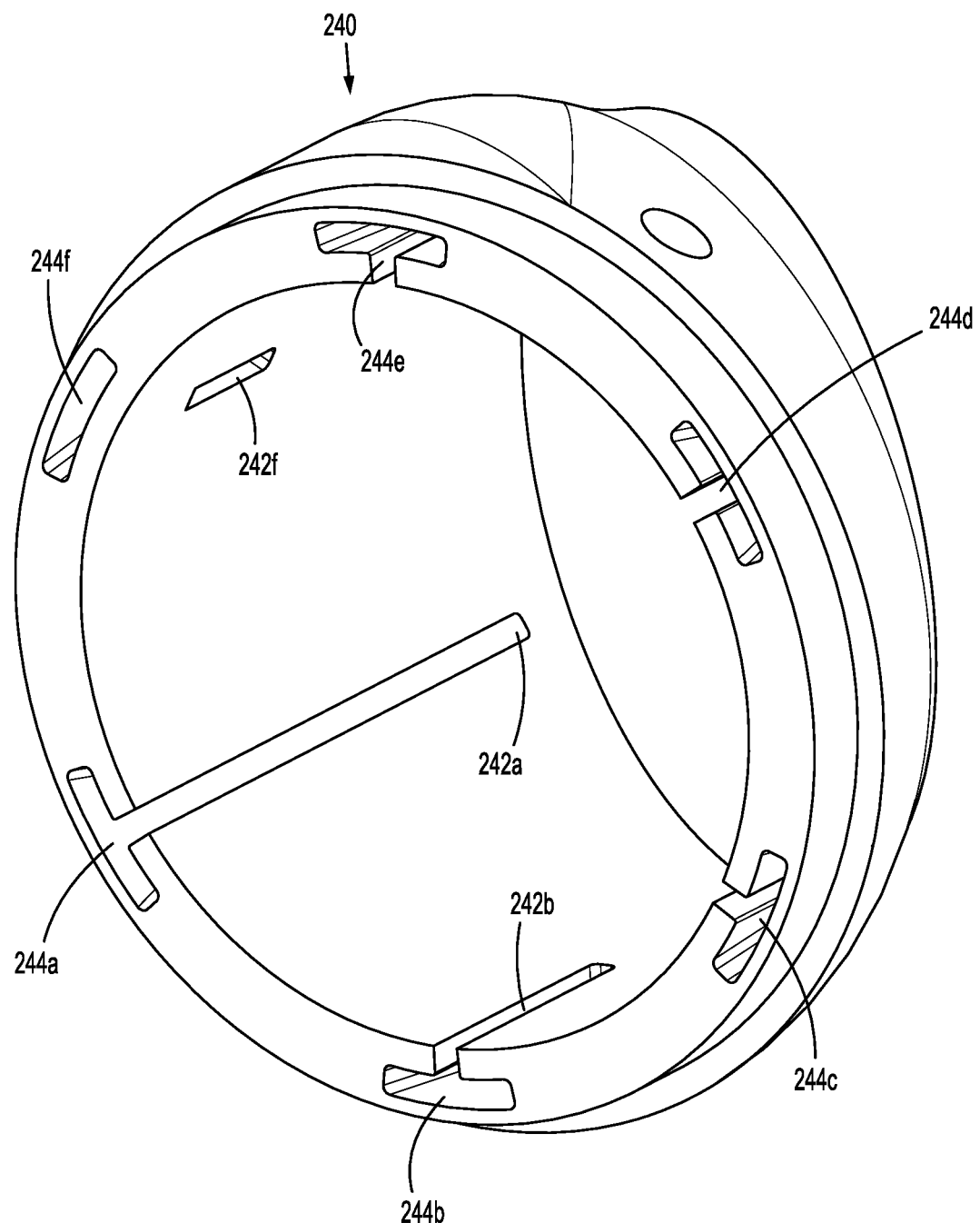
FIG. 6H is a rear perspective view of the distal tip of FIG. 6G.

With reference now to FIGS. 6G and 6H, the ports 142, 242 may not be in the same plane. In particular, one port 142, 242 may be closer to the outer wall 122 while an adjacent port 142, 242 may be closer to the inner wall 124 such that the ports 142, 242 are not on the same plane. It is also contemplated that this staggered arrangement may be repeated for all the ports 142, 242 where one or more ports are on one plane while other ports 142, 242 are on different planes (e.g., three ports located on three different planes). Other combinations of non-planar ports are also envisioned. Further, the ports 142, 242 may be arranged in a helical pattern and the ports 142, 242 may be angled with respect to the longitudinal axis of the surgical access device 100 to provide a desired spray pattern. Additionally, the ports 142, 242 may be staggered longitudinally.

Figure 13:
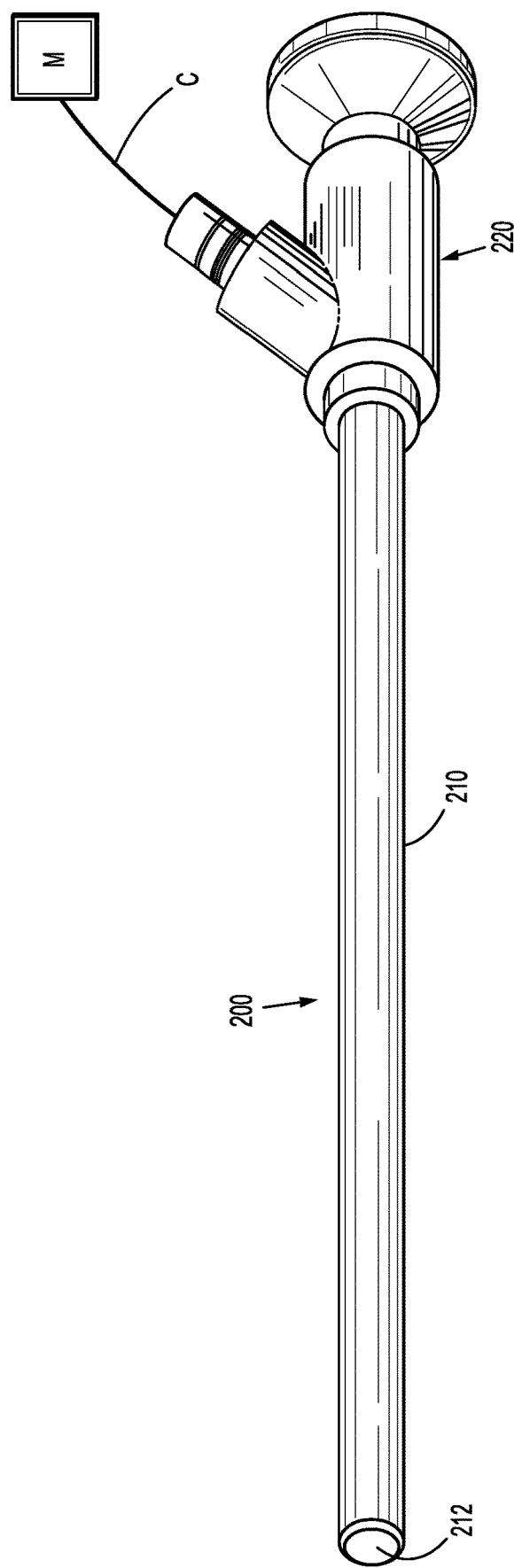
FIG. 13 is a perspective view of an endoscope.

The fluid flow in the predetermined region is usable to remove debris from an outer surface of a lens of a minimally invasive viewing instrument or an endoscope 200 (FIG. 13). The endoscope 200 has a housing 220 with a shaft 210 extending therefrom. A viewing element or lens 212 is located at the distal end of the shaft 210. A monitor M is coupled to the housing 220 of the endoscope 200 using cable C. The monitor M allows the clinician to see what is within the field of view of the lens 212 of the endoscope 200. This allows the clinician to observe the surgical site. During a surgical procedure, the endoscope 200 extends through the surgical access device 100 such that the lens 212 is in position in the surgical site providing the clinician with a view of the surgical site on the monitor M. When the lens 212 of the endoscope 200 is to be cleaned, the clinician moves the lens 212 of the endoscope 200 from the surgical site into the chamber 118 of the tubular member 120 such that an outer surface of the lens 212 is in the predetermined region such that the fluid directed into the predetermined region by the outlets 146a-f of the ports 142a-f impinges upon the outer surface of the lens 212 to gently dislodge particulate debris without damaging the outer surface of the lens 212. Additionally or alternatively, the clinician may move the endoscope 200 distally and proximally into and out of the predetermined region to assist removing debris from the lens 212. During the movement of the endoscope 200, the clinician may check the monitor to locate the position of the lens 212 relative to the predetermined region. This allows the clinician to more accurately position the lens 212 of the endoscope 200 for cleaning and also determine when the lens 212 of the endoscope is sufficiently cleaned. This may be performed with or without a change in the flow rate of fluid into the predetermined region to assist in cleaning debris from the lens 212. This cleans the outer surface of the lens 212 such that the clinician has an unobstructed view through the lens 212 of the endoscope 200. This arrangement allows the clinician to clean the lens 212 of the endoscope 200 without removing the endoscope 200 from the surgical site. As cleaning the lens 212 of the endoscope 200 may occur dozens of times during a surgical procedure, being able to clean the lens 212 without removing the endoscope 200 from the access device will streamline the surgical procedure allowing the clinician to perform the surgical procedure more efficiently and in less time as compared to removing the endoscope 200 multiple times during a procedure to clean it. Additionally, allowing the endoscope 200 to remain in the access device for cleaning reduces the risk of damaging the zero closure seal during repeated removals and insertions of the endoscope 200 for cleaning.

As assembled for use, fluid travels from the source of fluid FS through tubing to the inlet of the valve 150. Repositioning the lever 152 of the valve 150 controls the rate of fluid flow through the valve 150 from zero flow (i.e., valve 150 is fully shut) to full flow (i.e., valve 150 is fully open). With the valve 150 either partially or fully open, the fluid flows through the body of the valve 150 and exits the outlet 156 of the valve 150 where it enters the annular conduit 174 of the collar 170. The annular conduit 174 is fluidly coupled to the lumens 126a-f defined between the inner and outer walls 122, 124 of the tubular member 120 such that fluid exiting the outlet 156 of the valve 150 is directed by the annular conduit 174 to the lumens 126a-f and ultimately to the outlets 146a-f of the ports 142a-f. Although fluid flow is described as traveling from the source of fluid FS to the outlets 146a-f of the ports 142a-f, it is contemplated that fluid may flow from the outlets 146a-f of the ports 142a-f towards the valve 150 and an associated vacuum source or fluid source FS with a lower pressure than the pressure at the outlets 146a-f of the ports 142a-f.

Figure 14A:
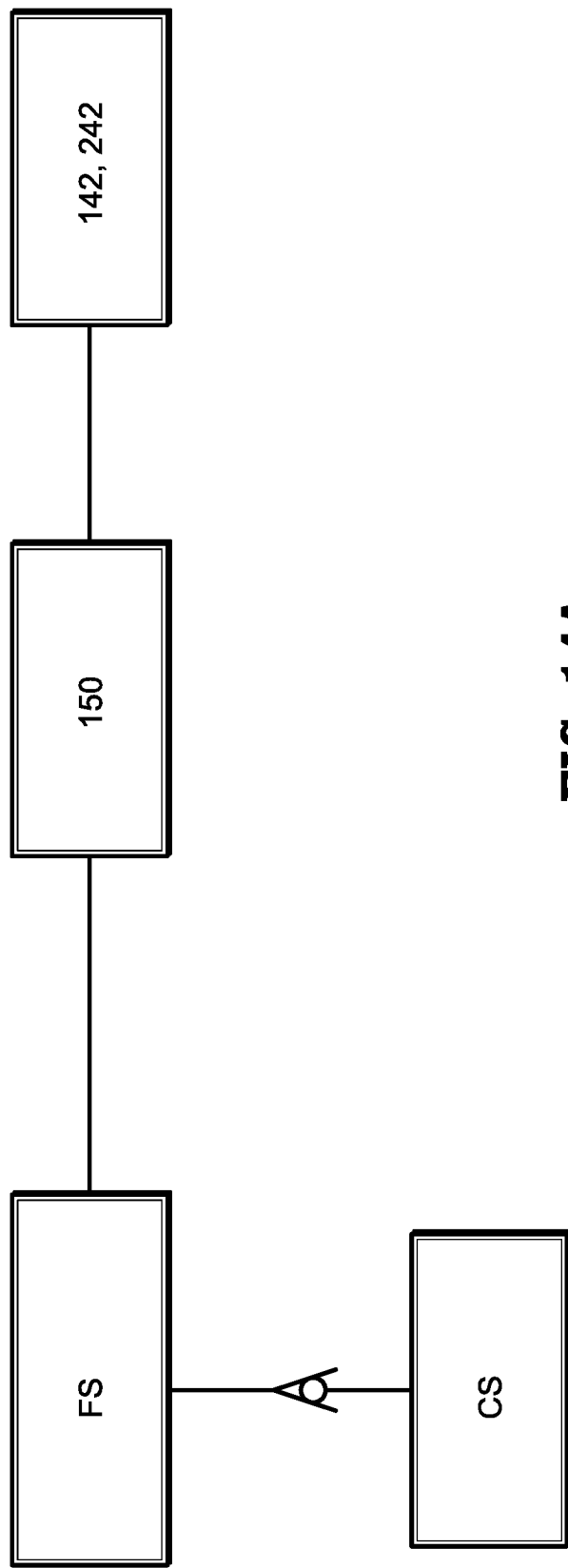
FIG. 14A is a schematic diagram of a flow path for insufflation and cleaning fluids.
Figure 14B:
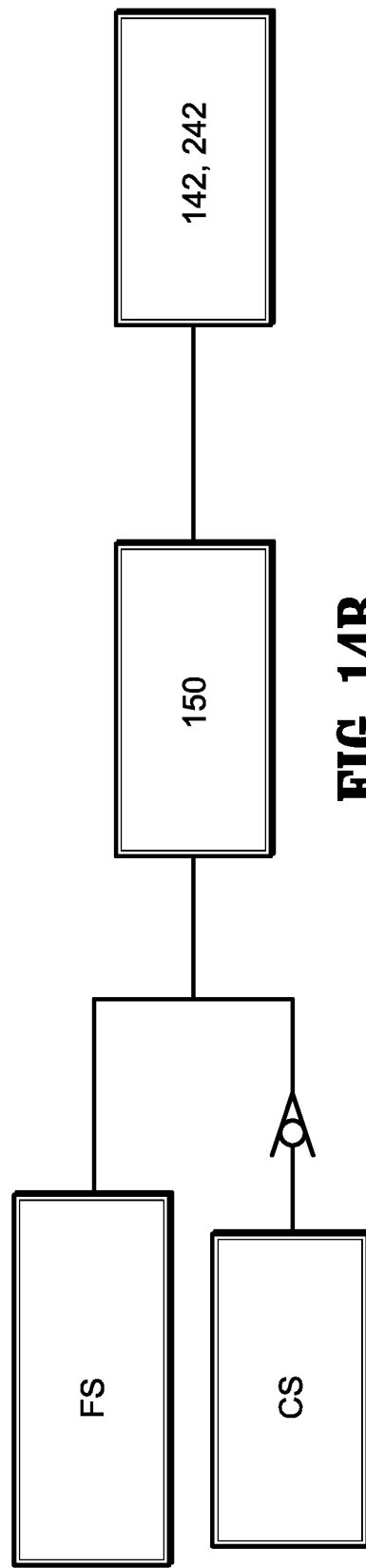
FIG. 14B is a schematic diagram of an alternate flow path for insufflation and cleaning fluids.
Figure 14C:
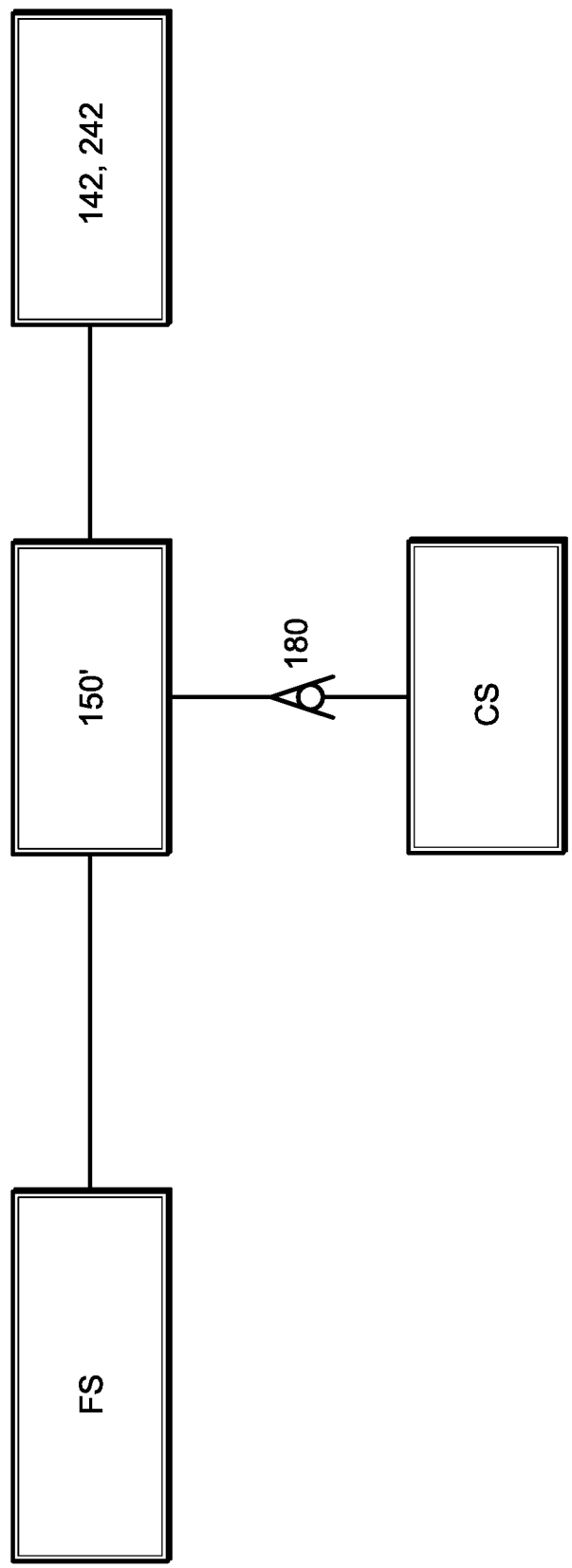
FIG. 14C is a schematic diagram of another flow path for insufflation and cleaning fluids.

FIGS. 14A-C illustrate various flow paths for fluid between the fluid source FS and the ports 142a-f, 242a-f of their respective tip members 142, 242 (FIGS. 6, 6A). As illustrated in FIG. 14A, the fluid source FS is a source of insufflation fluid (e.g., $CO_2$) with a fluid output that is coupled to the port 168 (FIG. 2) via the valve 150. A source (e.g., a squeeze bulb) of a cleaning fluid (e.g., saline) CS is coupled to the fluid source FS through a check valve 180. As the source of cleaning fluid CS is in-line (i.e., serial connection) with the fluid source FS, the check valve 180 allows the cleaning fluid to be injected into the flow path for the insufflation fluid while preventing the insufflation fluid from entering the source of cleaning fluid CS. The input to the valve 150 is insufflation fluid, insufflation fluid mixed with the cleaning fluid, or cleaning fluid. Once the particular fluid or fluids enter the port 168 (FIG. 2) via valve 150, the fluid or fluids are communicated to the ports 142a-f, 242a-f via lumens 126a-f (FIG. 4). In another embodiment shown in FIG. 14B, the fluid source FS and the source of cleaning fluid CS are disposed in a parallel configuration. As in the embodiment of FIG. 14A, the output of the source of cleaning fluid CS includes check valve 180 to prevent insufflation fluid from entering the source of cleaning fluid CS. Similar to the embodiment of FIG. 14A, the output of either the fluid source FS or the source of cleaning fluid CS is coupled to the port 168 (FIG. 2) via the valve 150. Akin to the embodiment of FIG. 14A, this arrangement allows insufflation fluid, a mixture of insufflation fluid and cleaning fluid, or cleaning fluid to be delivered to the port 168 (FIG. 2) via the valve 150. As before, the particular fluid or fluids enter the port 168 (FIG. 2) via valve 150 and are then communicated to the ports 142a-f, 242a-f via lumens 126a-f (FIG. 4). In a further embodiment shown in FIG. 14C, the fluid source FS and the source of cleaning fluid CS are independently coupled to a valve 150'. Valve 150' is a three-way valve with separate input connections for the insufflation fluid and the cleaning fluid. As in the previous embodiments, the connection between the source of cleaning fluid CS and the valve 150' includes check valve 180 that allows the source of cleaning fluid CS to supply cleaning fluid while preventing insufflation fluid from entering the source of cleaning fluid CS. The valve 150' allows the user to select between supplying insufflation fluid, supplying cleaning fluid, or supplying a mixture of insufflation and cleaning fluids. As in the previous embodiments, the particular fluid or fluids are delivered to the port 168 (FIG. 2) via the valve 150' and are then communicated to the ports 142a-f, 242a-f via lumens 126a-f (FIG. 4). Either the fluid source FS or the source of cleaning fluid CS may include a heater and pump for heating the cleaning fluid (e.g., saline). The heater may be a blood warmer or an on-demand heater.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical access device comprising:
a housing including a seal;
a tubular member extending from the housing, the tubular member including a plurality of lumens extending therethrough and inner and outer tubes that define an annular chamber therebetween, the plurality of lumens disposed within the annular chamber and radially spaced apart;
a valve disposed on the housing and fluidly coupled with the plurality of lumens; and
a tip member disposed at a distal end of the tubular member, the tip member including first and second ports aligned and fluidly coupled with respective first and second lumens of the plurality of lumens, the first port including a cavity having a tapered configuration extending between a proximal region and a distal region, the proximal region having a first width and the distal region having a second width less than the first width and configured to direct fluid flow towards a central longitudinal axis of the tubular member, the second port including a pocket extending between proximal and distal regions thereof, the pocket having a uniform width, the tip member having an open distal end configured to allow passage of an endoscope therethrough.

2. The surgical access device of claim 1, wherein a velocity of a fluid exiting the first port is greater than a velocity of a fluid exiting the second port.

3. The surgical access device of claim 1, wherein a first duct of the first port has a length equal to a length of a second duct of the second port.

4. The surgical access device of claim 1, wherein the tapered configuration of the cavity increases a velocity of a fluid passing from the proximal region of the first port to the distal region of the first port.

5. The surgical access device of claim 4, wherein a portion of the distal region of the first port is angled towards the central longitudinal axis of the tubular member such that fluid flow through the first port is directed towards the central longitudinal axis of the tubular member.

6. The surgical access device of claim 1, wherein the first port is offset from the second port by 180°.

7. The surgical access device of claim 1, wherein the first port and the second port are radially offset in a range between about 60° and about 120°.

8. The surgical access device of claim 1, further including a third port aligned and fluidly coupled to a third lumen of the plurality of lumens, the third port having a cavity with a tapered configuration comparable to the tapered configuration of the first port.

9. The surgical access device of claim 8, wherein the first port is spaced a first distance from the central longitudinal axis of the tubular member and the third port is spaced a third distance from the central longitudinal axis of the tubular member, the first distance different from the third distance.

10. The surgical access device of claim 1, wherein the tubular member defines a channel extending therethrough, the channel configured to receive a viewing instrument therethrough.

* * * * *